United States Patent [19]

Matsumoto et al.

[11] 4,096,048

[45] Jun. 20, 1978

[54] OXYGEN SENSOR AND MANUFACTURING METHOD THEREOF

[75] Inventors: Shinichi Matsumoto, Toyota; Hirohisa Miura, Okazaki; Kiyoshi Uchida; Yasuhiro Otsuka, both of Toyota, all of Japan

[73] Assignee: Toyota Jidosha Kogyo Kabushiki Kaisha, Japan

[21] Appl. No.: 805,109

[22] Filed: Jun. 9, 1977

[30] Foreign Application Priority Data

Oct. 26, 1976   Japan ................................ 51-128627

[51] Int. Cl.² ............................................. G01N 27/46
[52] U.S. Cl. .................................. 204/195 S; 29/592 R
[58] Field of Search ............... 204/1 S, 195 S; 60/276; 123/119 E; 73/23; 324/29, 71 R; 29/592, 595

[56] References Cited

U.S. PATENT DOCUMENTS

| | | | |
|---|---|---|---|
| 3,481,855 | 12/1969 | Kolodney et al. | 204/195 S |
| 3,576,730 | 4/1971 | Spacil | 204/195 S |

FOREIGN PATENT DOCUMENTS

| | | | |
|---|---|---|---|
| 2,304,464 | 8/1974 | Germany | 204/195 S |

Primary Examiner—G. L. Kaplan
Attorney, Agent, or Firm—Oblon, Fisher, Spivak, McClelland & Maier

[57] ABSTRACT

An oxygen sensor consisting of a metal electrode formed on the surface of the side to be measured of a solid electrolyte sintering and of a reference oxygen pole formed by a mixture of metal and metal oxide on the opposite side of said surface of the side to be measured of the solid electrolyte sintering body, characterized in that, at least over the whole surface adjoining the mixture of metal and metal oxide on the side of the reference oxygen pole of the solid electrolyte sintering, a porous metal electrode is formed to insulate the solid electrolyte sintering from the mixture of metal and metal oxide, thereby improving the low temperature performance and internal impedance characteristics, as well as prolonging the life thereof. A method for manufacturing this sensor is also provided.

11 Claims, 7 Drawing Figures

OXYGEN SENSOR AND MANUFACTURING METHOD THEREOF

BACKGROUND OF THE INVENTION

1. Field of the Invention

The present invention relates generally to an oxygen sensor for detecting the oxygen concentration in the exhaust gas of an automobile engine, and more particularly to such an oxygen sensor to be employed in a system capable of simultaneously disposing of the harmful elements in the engine exhaust of an automobile, such as the unburnt hydrocarbons, nitrogen oxides and carbon monoxide, through reaction with a catalyst, and to a method of manufacturing the oxygen sensor.

2. Description of the Prior Art

An oxygen sensor uses a solid electrolyte sintering of an oxygen ion-conductive ceramic material as a partition wall and the oxygen concentration ratio in two spaces divided by this wall is converted to an electromotive force. As is well known, designating the partial pressure of oxygen in one of the spaces as $Po_2(1)$ and that in the other spaces as $Po_2(2)$, the electromotive force E generated between the electrodes formed on both sides of the partition wall will be given by:

$$E = \frac{RT}{4F} \ln \frac{Po_2(1)}{Po_2(2)},$$

where R is a gas constant, T is the absolute temperature, and F is the Faraday constant. Thus when $Po_2(1)$ is known, the unknown $Po_2(2)$ can be found by measuring the electromotive force E.

In the conventional oxygen sensor, the equilibrium oxygen partial pressure of the atmosphere, or of a mixture of metal and metal oxide, has been used as the oxygen source of known concentration, that is, $Po_2(1)$. Generally speaking, the following drawbacks have been complained of by users of the conventional oxygen sensor. For instance, in the sensor utilizing the atmosphere as the reference oxygen pole, the mechanism is complicated because an atmosphere inlet tube has to be provided, and invasion of water or mud into such a tube has to be prevented. Further, in the sensor utilizing a mixture of metal and metal oxide as the reference oxygen pole, a long, continuous and stable service of the sensor cannot be expected on account of the metal and metal oxide mixture of Ni/NiO, Cu/CuO, Co/CoO and Fe/FeO, which are known to be available for this purpose, being oxidized or reduced through exposure to the exhaust gas, or of this metal and metal oxide mixture reacting with a solid electrolyte. Furthermore, when such a solid reference oxygen pole is employed as the reference pole, the low temperature performance drops, as for example, at less than 400° C, an electromotive force does not develop, or on account of an increased internal impedance, an apparent drop in the electromotive force occurs, which is a great drawback of this sensor as compared with one utilizing the atmosphere as the reference oxygen pole.

SUMMARY OF THE INVENTION

An object of the present invention is to provide an oxygen sensor in which a solid electrolyte and a mixture of metal and metal oxide can remain for a long time in the exhaust gas without reacting with each other.

Another object of the present invention is to provide an oxygen sensor of excellent low temperature performance which can develop an electromotive force even in the low temperature range.

Still another object of the present invention is to provide an oxygen sensor of excellent internal impedance characteristics in which the internal impedance is low in the acting range.

Yet another object of the present invention is to provide a method of manufacturing an oxygen sensor of the type described.

BRIEF DESCRIPTION OF THE DRAWINGS

Various other objects, features and attendant advantages of the present invention will be more fully appreciated as the same becomes better understood from the following detailed description when considered in connection with the accompanying drawings, in which like reference characters designate like or corresponding parts throughout the several views and wherein.

DESCRIPTION OF THE PREFERRED EMBODIMENTS

Figure 1:
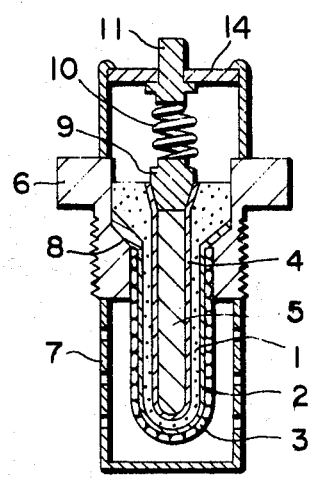
FIG. 1 is a sectional view of an oxygen sensor according to the present invention.

Referring now to the drawings, and more particularly to FIG. 1, in which there is illustrated the basic constitution of the oxygen sensor according to the present invention, the oxygen sensor is shown being comprised of a solid electrolyte sintering 1 made of an oxygen ion-conductive ceramic material, a porous external metal electrode 2 formed in a layer on the surface of the side of the solid electrolyte sintering 1 to be measured, a porous coating layer 3 of inorganic material formed on the external metal electrode 2 (the sensor can function, however, even without the porous coating layer 3), an internal metal electrode 4 formed in a layer on the opposite side of the solid electrolyte sintering 1 for the purpose of insulating the solid electrolyte sintering 1 from a mixture of metal and metal oxide charged therein, and a reference oxygen pole 5 made of the mixture of metal and metal oxide charged and sintered in the solid electrolyte sintering 1, the solid electrolyte sintering 1 being supported by a holder 6 and provided with a means to take out the output from the internal metal electrode 4.

To complete the functioning of the oxygen sensor having the above structure, a porous protective cover 7, for the electrode, is provided on the outside of the solid electrolyte sintering 1 which has an external metal electrode 2, and, depending on the case, even a porous coating layer 3, formed thereon. Meanwhile, between the external metal electrode 2 and the holder 6 there is inserted an electric conductor, say, a graphite sheet 8, so that an electric signal from the external metal electrode 2 may be transmitted to the holder 6 and then grounded to the car body. While the means to take out the output from the internal metal electrode 4 may be of any structure that can effectively take out the output, as an example, the structure may be such that it comprises an output take-out tip 9 connected to the internal metal electrode 4, a coil spring 10 which connects the tip 9 to the internal metal electrode 4 and at the same time connects the electrolyte sintering 1 to the holder 6, and an output terminal 11 which serves to take out the output signal coming via the output take-out tip 9 and the coil spring 10. The output terminal 11 which connects a coil spring 10 to the internal metal electrode 4 is insulated electrically by the insulator 14 from the sensor holder 6 connected to the external metal electrode 2.

Figure 2:
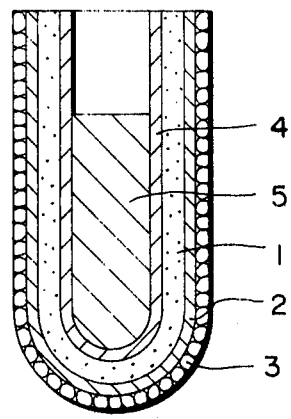
FIG. 2 is an enlarged sectional view of the electromotive force developing part of the oxygen sensor in FIG. 1, the part being those of the samples A, C, D, E in Examples 1, 3, 4, 5, herein.

Next, a further detailed description of each component will be made. In FIG. 2, the solid electrolyte sintering 1 may be made of anything which is oxygen ion-conductive, for example, $ZrO_2$—CaO. MgO, $Y_2O_3$, $Sc_2O_3$ and $Nd_2O_3$ are available instead of CaO, and $HfO_2$, $CeO_2$, $UO_2$ and $ThO_2$ can be used instead of $ZrO_2$.

The porous metal electrodes 2 and 4 can be a porous layer of any antioxidizing material with catalyst activity, as for example, Pt singly or as blended with Pd, Au or Rh is available, the thickness being desirable in the range of $0.5\mu \sim 20\mu$. Among these, the internal metal electrode 4, being aimed at perfect insulation of the solid electrolyte sintering 1 from the mixture of metal and metal oxide charged therein, is provided, covering at least the whole surface of the solid electrolyte sintering where the reference oxygen pole adjoins the mixture 4 of metal and metal oxide.

The inorganic substances available for forming the porous coating layer 3 include, for instance, the stabilizing $ZrO_2$, $Al_2O_3$, and $MgO.Al_2O_3$, the thickness of the layer being desirably in the range of $5\mu \sim 250\mu$.

Figure 3:
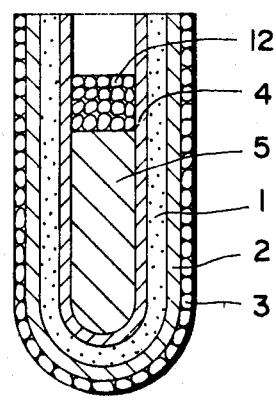
FIG. 3 is an enlarged sectional view of the Sample B, which is the electromotive force developing part of the oxygen sensor in Example 2.

The reference oxygen pole 5 of a mixture of metal and metal oxide may be obtained by sintering Fe/FeO, Ni/NiO, Cu/CuO or Co/CoO. Thereby, as illustrated in FIG. 3, the solid electrolyte sintering 1 may be formed as a vessel, into which the reference oxygen pole 5 may be inserted, and then a heat-resistant inorganic substance 12 may be charged through an opening of the vessel and sintered.

Next some practical examples of manufacturing the oxygen sensor are cited.

EXAMPLE 1

A solid electrolyte sintering 1 of 90 mol % $ZrO_2$ - 10 mol % $Y_2O_3$ system was well degreased with acetone, followed by etching through 20 minutes of immersion at 40° C in an aqueous solution composed of chromic anhydride 50 g/l, sulfuric acid 100 ml/l and hydrofluoric acid 100 ml/l. After full washing with water, the sintering was dipped for several seconds in an aqueous solution of chloroplatinic acid 5 g/l at room temperature, and then dried at 50° C for 30 minutes. The dried sintering was next immersed at room temperature for 10 minutes in an aqueous solution of sodium borohydride 3 g/l. After this preliminary treatment for precipitation-nucleus formation, the sintering was immersed in a plating solution of 0.25 g of chloroplatinic acid in 950 ml of concentrated aqueous solution of ammonia, which had been diluted with pure water to the total volume of 1l and further had added thereto 0.18 sodium borohydride, just before use. After left for 2 hours at a bath temperature of 25° C, platinum was uniformly precipitated on the surface of the solid electrolyte sintering 1. Thereafter, using a commercial electrolytic platinum plating solution (platinum plating solution No. 745 of Japan Englehard Co.), plating was done for 20 minutes under these conditions: platinum concentration 12 g/l, current density 0.8 A/dm², bath temperature 80° C, and pH 12.5, yielding porous metal electrodes 2 and 4 of thickness $2\mu$. Then, on the porous metal electrode 2 was formed a porous coating layer 3 of about $100\mu$ thickness, by plasma metallization of alumina powder. Plasma metallization was done under the conditions: plasma arc current 500A, arc voltage 65V, gases and gas flow rates $N_2$ 100 SCFH and $H_2$ 15 SCFH and powder feed rate 5.5 lb/hr. Next, Fe powder and $Fe_2O_3$ powder (both commercial reagents) were blended together at a mol ratio of 1 : 1; placed in an alumina tube to be heated for about 2 hours, at 1000° C in a argon stream, then left to cool and again turned to powder, which was charged into the solid electrolyte sintering 1 to be sintered for 1 hour at 1000° C in an argon stream.

The sintering temperature of the metal/metal oxide mixture need not be limited to 1000° C, but the desirable range is 600°0 C $\sim$ 1400° C. At less than 600° C, it takes time for sintering, but at more than 1400° C, the risk of the solid electrolyte sintering 1 being broken is high. When sintering at around 1000° C, the time will be about 1 $\sim$ 3 hours. The element thus obtained (as illustrated in FIG. 2) was assembled together with other elements to produce an oxygen sensor. The oxygen sensor thus produced is designated as the sample A.

EXAMPLE 2

The same element, as in Example 1, was produced and, as illustrated in FIG. 3, a heat-resistant inorganic substance 12 was laid over Fe/FeO powder. Using alumina powder and "Ceramacast" (a kind of heat-resistant alumina cement) as the heat-resistant inorganic substance 12, 1 hour of sintering was done at 300° C in the air. The element thus yielded (as illustrated in FIG. 3) was combined with other elements such as the holder 6 and the like to produce an oxygen sensor. The oxygen sensor thus obtained is designated as the sample B.

EXAMPLE 3

In the same way as in Example 1, a solid electrolyte sintering 1 of 90 mol % $ZrO_2$ - 10 mol % $Y_2O_3$ system was etched, fully washed with water and dried. Next, a commercial paste was applied with a brush on both sides of the solid electrolyte sintering 1, and through 30 minutes of sintering at 800° C in the air in an electric furnace, about 3 $\mu$ thick porous metal electrodes 2 and 4 were formed. Just as in Example 1, a blend of commercial Fe powder and $Fe_2O_3$ powder was reacted, crushed and then charged for sintering into the solid electrolyte sintering 1. The oxygen sensor thus produced is designated as the sample C.

EXAMPLE 4

Using the same solid electrolyte sintering 1 of 90 mol % $ZrO_2$ - 10 mol % $Y_2O_3$ system as in Example 1, platinum electrodes 2 and 4 were formed by chemical and electric platings on both sides of the sintering 1. Next, commercial Ni powder (purity 99.9%) and commercial special grade reagent NiO powder were blended at a mol ratio of 1 : 1 and sintered for 24 hours at 1000° C in an argon atmosphere. The product was crushed and charged into the sintering 1 for 1 hour of sintering at 1000° C in an argon atmosphere, the process otherwise being the same as in Example 1. The oxygen sensor thus obtained is designated as the sample D.

EXAMPLE 5

Instead of Ni powder and NiO powder, in Example 4, a blend at mol ratio 2 : 1 of commercial Co powder (purity 99.5%) and commercial special grade reagent CoO powder was employed and provided the same heat treatment as in Example 4, thereby yielding an oxygen sensor. The oxygen sensor thus yielded is designated as the sample E.

Manufacture of a comparison sample F

For the purpose of comparison in performance of the oxygen sensor according to the present invention, a sample F, exhibiting the characteristics of the conventional oxygen sensor, was manufactured by the following method.

Figure 4:
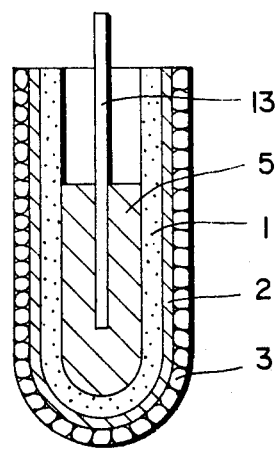
FIG. 4 is an enlarged sectional view of the comparison sample F, corresponding to the conventional oxygen sensor.

Under the same conditions as in Example 1, Pt electrode was formed on only the outside surface of the same solid electrolyte sintering as in Example 1. Then, as illustrated in FIG. 4, under the same conditions as in Example 1, a metal/metal oxide mixture was charged into the solid electrolyte sintering 1, while at the same time a Pt electrode wire 13 for the electrode (diameter of wire 0.5 mm) was buried therein, for sintering. The oxygen sensor thus obtained is designated as the comparison sample F.

Using the samples A, B, C, D and E, tests were made to investigate the various characteristics of the oxygen sensor according to the present invention. In these tests, the comparison sample F was also investigated, to compare the same with the oxygen sensor according to the present invention and to clarify its characteristics.

With the temperature dependency of the internal resistance, the loading characteristic and the temperature of the oxygen sensor being held constant, $N_2$ with 1% dry air contained therein was passed at a rate of 2 l/min through the external electrode 2 of the sensor, and the sensor terminal voltage, when a known load resistance was connected in series to the sensor, was measured by a millivoltmeter of input impedance 1000 M $\Omega$. The internal resistance of the sensor was calculated from the voltage drop when the volume of the current flowing in the load resistance was in the range of 0.1 mA $\sim$ 0.5 mA.

Figure 5:
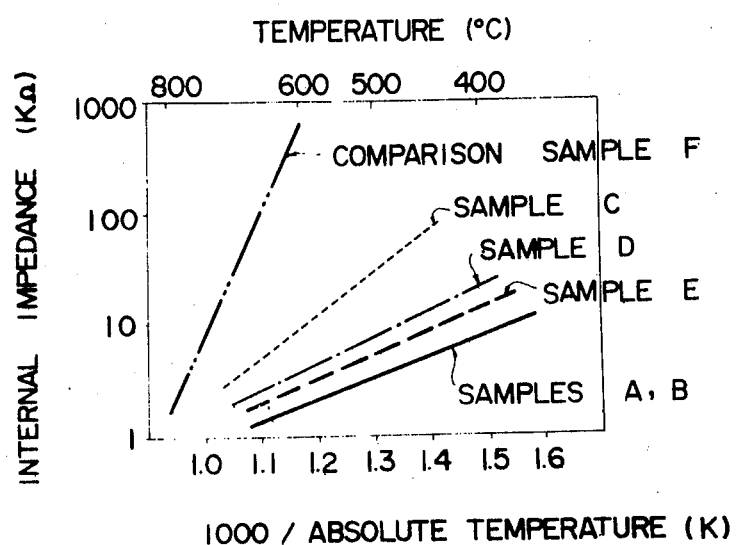
FIG. 5 is a temperature vs. internal impedance characteristic diagram of the samples A, B, C, D, E and F.
Figure 6:
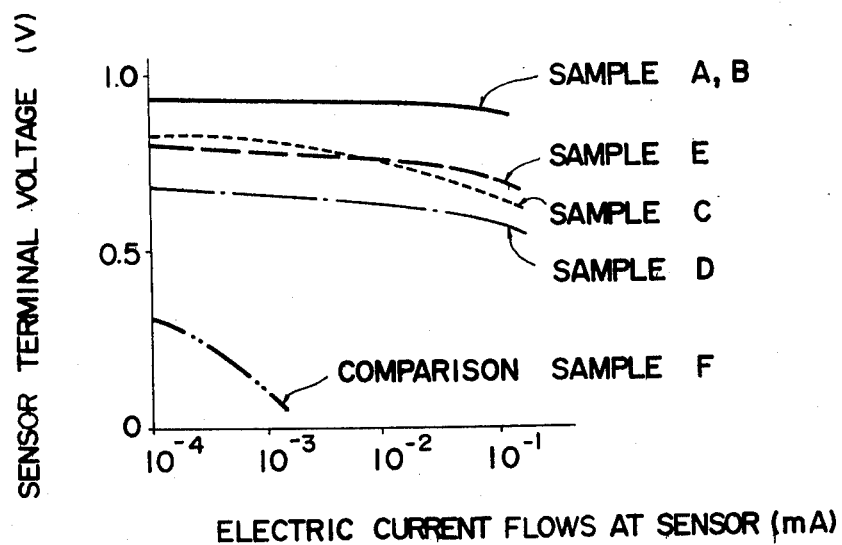
FIG. 6 is a current vs. terminal voltage characteristic diagram of the samples A, B, C, D, E and F.

The test results on the temperature dependency of internal resistance of the oxygen sensor are summarized in FIG. 5 and the test results on the loading characteristic in FIG. 6. From these results it is seen how superior, in both the internal impedance and the loading characteristic, the oxygen sensor of the present invention is to the comparison sample F.

As to temperature dependency of electromotive force of the oxygen sensor, in the same way as in the test (a), a gas was passed to the external electrode side of the oxygen sensor, and then the sensor was heated at a rising temperature rate of 20° C/min. The electromotive force generated thereby in the sensor was measured by a millivoltmeter of input impedance 1000 M $\Omega$.

Figure 7:
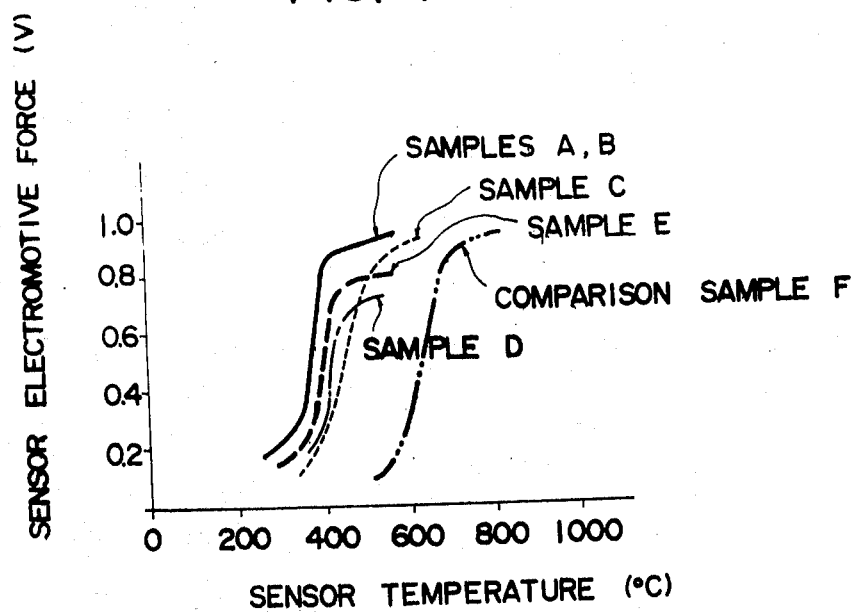
FIG. 7 is a sensor temperature vs. sensor electromotive force characteristic diagram of the samples A, B, C, D, E and F.

The results are summarized in FIG. 7, from which it is seen how much improved is the low temperature performance of the oxygen sensor according to the present invention.

As to the service life of the oxygen sensor, the time taken for the electromotive force to drop to 0.5V when the oxygen sensor was heated at 1000° C in the air was defined as its service life and this life was measured with each sample, the results being illustrated in Table 1.

TABLE 1

| Samples | Life (hours) |
| --- | --- |
| Sample A | 400 |
| Sample B | 500 |
| Sample C | 350 |
| Sample D | 380 |
| Sample E | 360 |
| Comparison sample F | 250 |

It is evident from the above Table that the life of the oxygen sensor according to the present invention is extremely improved.

Moreover, as the result of the solid electrolyte sintering 1 and the metal/metal oxide mixture 5 being perfectly insulated from each other through the metal electrode 4 formed extensively between them, the life has been improved remarkably, even in the case of $ZrO_2$ sintering, in which $Y_2O_3$ is employed as a stabilizer easy to react with the Fe compound.

From the above tests, the effects of the oxygen sensor according to the present invention are obvious, in that remarkable improvements are gained in the internal resistance, the loading characteristic, the low temperature performance and the service life.

Obviously, many modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. An oxygen sensor comprising:
   a solid electrolyte sintering of an oxygen ion-conductive ceramic material;
   a metal electrode formed on the measured side of said solid electrolyte sintering;
   a reference oxygen pole of a mixture of metal and metal oxide charged on the opposite side of said solid electrolyte sintering;
   a metal electrode formed on the side of said reference oxygen pole covering at least the total area of said solid electrolyte sintering which adjoins said reference oxygen pole, said metal electrode serving to insulate said reference oxygen pole from said solid electrolyte sintering;
   a holder to support said solid electrolyte;
   and a means to take out the outputs of said two metal electrodes.

2. An oxygen sensor as set forth in claim 1, wherein a porous coating layer of inorganic substance is provided, covering the metal electrode, on the surface of the measured side of said solid electrolyte sintering.

3. An oxygen sensor as set forth in claim 2, wherein said porous coating layer is 5 $\mu$ $\sim$ 250 $\mu$ thick.

4. An oxygen sensor as set forth in claim 1, wherein said solid electrolyte sintering is formed like a vessel and a heat-resistant inorganic substance, charged and sintered, is provided at the vessel opening side of said reference oxygen pole charged into said vessel.

5. An oxygen sensor as set forth in claim 1, wherein the metal electrode on the side of the reference oxygen pole and the metal electrode on the side of measured system are respectively 0.5 $\mu$ $\sim$ 20 $\mu$ thick.

6. An oxygen sensor as set forth in claim 1, wherein said solid electrolyte is a composition of at least one from among the group consisting of $ZrO_2$, $H_5O_2$ and $CeO_2$ and at least one from the group of CaO, MgO, and $Y_2O_3$.

7. An oxygen sensor as set forth in claim 1, wherein the metal electrode on the side of the reference oxygen pole and the metal electrode on the side of the measured system are, respectively, made of Pt alone or a combination of Pt and at least one from among Pd, Au and Rh.

8. An oxygen sensor as set forth in claim 1, wherein said reference oxygen pole is constituted of one from among the group consisting of Ni/NiO, Cu/CuO, Co/CoO and Fe/FeO.

9. A manufacturing method of an oxygen sensor, comprising the steps of:

forming a solid electrolyte sintering of an oxygen ion-conductive inorganic substance;

forming a metal electrode on each side of said solid electrolyte sintering by electric plating or by pasting;

forming a reference oxygen pole by charging and sintering a mixture of metal and metal oxide on one part of the solid electrolyte in such a manner that said oxygen pole may be insulated by said metal electrode from said solid electrolyte sintering; and assembling said solid electrolyte sintering with a holder and a means to take out the outputs of both metal electrodes.

10. A manufacturing method as set forth in claim 9, further comprising the step of forming a porous coating layer, by plasma metallization of an inorganic substance, on the metal electrode opposite to the reference oxygen pole of said solid electrolyte sintering.

11. A manufacturing method as set forth in claim 9, wherein said solid electrolyte sintering is formed like a vessel, said reference oxygen pole is charged and sintered in said vessel, and then a heat-resistant inorganic substance is charged and sintered at the vessel opening side of said reference oxygen pole.

* * * * *